(12) United States Patent  (10) Patent No.: US 9,078,984 B2
Poon et al.  (45) Date of Patent: Jul. 14, 2015

(54) MECHANICAL VENTILATOR

(75) Inventors: Chi-Sang Poon, Lexington, MA (US);
Gang Song, Malden, MA (US); Shawna M. MacDonald, Cambridge, MA (US)

(73) Assignee: Massachusetts Institute of Technology, Cambridge, MA (US)

(*) Notice: Subject to any disclaimer, the term of this patent is extended or adjusted under 35 U.S.C. 154(b) by 1239 days.

(21) Appl. No.: 12/362,915

(22) Filed: Jan. 30, 2009

(65) Prior Publication Data
US 2009/0194110 A1 Aug. 6, 2009

Related U.S. Application Data

(60) Provisional application No. 61/025,044, filed on Jan. 31, 2008.

(51) Int. Cl.
*A62B 7/04* (2006.01)
*A61M 16/00* (2006.01)

(52) U.S. Cl.
CPC ..................................... *A61M 16/00* (2013.01)

(58) Field of Classification Search
USPC ............. 128/204.26, 200.11, 200.26, 203.12, 128/203.15, 203.27, 204.18, 204.21, 128/204.23, 205.18, 205.25, 206.21, 128/207.14, 207.18
See application file for complete search history.

(56) References Cited

U.S. PATENT DOCUMENTS 4,281,651 A * 8/1981 Cox .......................... 128/204.23
5,692,497 A * 12/1997 Schnitzer et al. ........ 128/204.21
5,916,239 A * 6/1999 Geddes et al. ................... 607/14
6,390,091 B1 * 5/2002 Banner et al. ............ 128/204.21
6,463,327 B1 * 10/2002 Lurie et al. ....................... 607/42
6,557,553 B1 * 5/2003 Borrello .................... 128/204.18
2002/0123692 A1 * 9/2002 Pail ................................. 600/534
2005/0109340 A1 * 5/2005 Tehrani .................... 128/204.21

(Continued)

FOREIGN PATENT DOCUMENTS

WO WO 2007122406 A1 * 11/2007 ............ A61M 16/00

OTHER PUBLICATIONS

Allo, J. C. et al., "Influence of neurally adjusted ventilatory assist and positive end-expiratory pressure on breathing pattern in rabbits with acute lung injury," *Critical Care Medicine*, 34: 2997-3004, 2006.

(Continued)

*Primary Examiner* — Tan-Uyen (Jackie) T Ho
*Assistant Examiner* — Eric Bryant
(74) *Attorney, Agent, or Firm* — Hamilton, Brook, Smith & Reynolds, P.C.

(57) ABSTRACT

An entrainment-based mechanical ventilator may be initially set to approximate the patient's spontaneous respiratory frequency, enabling the patient to entrain to the ventilator if the ventilator frequency matches the patient's spontaneous breathing frequency or is within a reasonable range from it. If the preset frequency of the ventilator is set too high or too low from the spontaneous frequency, the patient will fall out of phase and "fight" the ventilator. The ventilator phase relative to the patient's breathing effort indicates the difference between the ventilator frequency and spontaneous frequency. Based on the phase difference, a closed-loop control mechanism may continuously adjust the ventilator frequency to match the patient breathing frequency until the phase shift is within a preset limit. Patient-ventilator entrainment will occur when the ventilator frequency is within a certain range from the patient breathing frequency.

16 Claims, 10 Drawing Sheets

(56) References Cited

U.S. PATENT DOCUMENTS

| | | | | |
|---|---|---|---|---|
| 2007/0028921 | A1* | 2/2007 | Banner et al. | 128/204.21 |
| 2007/0163590 | A1* | 7/2007 | Bassin | 128/204.23 |
| 2007/0215154 | A1* | 9/2007 | Borrello | 128/204.21 |
| 2008/0109045 | A1* | 5/2008 | Gross et al. | 607/39 |

OTHER PUBLICATIONS

Baconnier, P.F. et al., "Entrainment of the Respiratory Rhythm: A New Approach," *Journal of Theoretical Biology*, 164: 149-162, 1993.
Baumer, J.H., "International Randomized Controlled Trial of Patient Triggered Ventilation in Neonatal Respiratory Distress Syndrome," *Archive of Disease in Childhood Fetal Neonatal*, Edition 82: F5-F10, 2000.
Beresford, M.W. et al., "Randomized Controlled Trial of Patient Triggered and Conventional Fast Rate Ventilation in Neonatal Respiratory Distress Syndrome," *Archive of Disease in Childhood Fetal Neonatal*, Edition 82: F14-18, 2000.
Breuer, J., "Self-Steering of Respiration through the Nerves Vagus," Breathing: Hering-Breuer Centenary Symposium London: Churchill, pp. 365-394, 1970.
Brochard, L., "Intrinsic (or Auto-) PEEP During Controlled Mechanical Ventilation," *Intensive Care Medicine*, 28: 1376-1378, 2002.
Chao, D.C. et al., "Patient-Ventilator Trigger Asynchrony in Prolonged Mechanical Ventilation," *Chest*, 112: 1592-1599, 1997.
Dick, C.R. et al., "Patient-Ventilator Interactions," *Clinical Chest Medicine 17*: 423-438, 1996.
Gautier, H. et al., "Breuer-Hering inflation reflex and breathing pattern in anesthetized humans and cats," *Journal of Applied Physiology*, 51: 1162-1168, 1988.
Graves, C. et al., "Respiratory Phase Locking During Mechanical Ventilation in Anesthetized Human Subjects," *American Journal of Physiology*, 250: R902-909, 1986.
Grippi, M.A. et al., "Adaptation to Reflex Effects of Prolonged Lung Inflation," *Journal of Applied Physiology*, 58: 1360-1371, 1985.
Guz, A. et al., "Studies on the Vagus Nerves in Man: Their Role in Respiratory and Circulatory Control," *Clinical Science*, 27: 293-304, 1964.
Guz, A. et al., "Pulmonary Stretch Receptor Activity in Man: A Comparison with Dog and Cat," *Journal of Physiology*, 213: 329-343, 1971.
Haberthur, C. et al., "Short-Term Effects of Positive End-Expiratory Pressure on Breathing Pattern: An Interventional Study in Adult Intensive Care Patients," *Critical Care*, 9: R407-415, 2005.
Hamilton, R.D. et al., "The Effect of Lung Inflation on Breathing in Man During Wakefulness and Sleep," *Respiratory Physiology*, 73: 145-154, 1988.
Hamilton, R.D. et al., "Effect on Breathing of Raising End-Expiratory Lung Volume in Sleeping Laryngectomized Man," *Respiratory Physiology*, 81: 87-98, 1990.
Hering, E., "Self-Steering of Respiration through the Nerves Vagus," Breathing: Hering-Breuer Centenary Symposium London: Churchill, pp. 359-364, 1970.
Imanaka, H. et al., "Auto Triggering Caused by Cardiogenic Oscillation During Flow-Triggered Mechanical Ventilation," *Critical Care Medicine*, 28: 402-407, 2000.
Kondili, E. et al., "Patient-Ventilator Interaction," *British Journal of Anesthesia*, 91: 106-119, 2003.
Lumsden, T., "Observations on the Respiratory Centres in the Cat," *Journal of Physiology London*, 57: 153-160, 1923.
MacDonald, S.M. et al., "Nonassociative Learning Promotes Respiratory Entrainment to Mechanical Ventilation", PLoS ONE 2(9): e865. doi:10.1371/journal.pone.0000865, Sep. 12, 2007.
Mador, M.J. et al., "Apneustic Breathing. A Characteristic Feature of Brainstem Compression in Achondroplasia," *Chest*, 97: 877-883, 1990.
Matsugu, M. et al., "Entrainment, Instability, Quasi-Periodicity, and Chaos in a Compound Neural Oscillator," *Journal of Computational Neuroscience*, 5: 35-51, 1998.

McGuire M.S. et al., "Phrenic Long-Term Facilitation is Robust to Hypercapnia and Hypocapnia but not Hyperventilatory Hypotension Under PEEP," *Respiratory Physiology and Neurobiology*, 158: 107-111, 2007.
Muzzin, S. et al., "Entrainment of Respiratory Rhythm by Periodic Lung Inflation: Effect of Airflow Rate and Duration," *American Journal of Physiology*, 263: R292-300, 1992.
Muzzin, S. et al., "Entrainment of the Respiratory Rhythm by Periodic Lung Inflation During Vagal Cooling," *Respiratory Physiology*, 75: 157-172, 1998.
Oddo, M. et al., "Management of Mechanical Ventilation in Acute Severe Asthma: Practical Aspects," *Intensive Care Medicine*, 32: 501-510, 2006.
Pepe, P.E. et al., "Occult Positive End-Expiratory Pressure in Mechanically Ventilated Patients with Airflow Obstruction: The Auto-PEEP Effect," *American Review of Respiratory Disease*, 126: 166-170, 1982.
Petrillo, G.A. et al., "Phase Locking of the Respiratory Rhythm in Cats to a Mechanical Ventilator," *Canadian Journal of Physiology and Pharmacology*, 61: 599-607, 1983.
Petrillo, G.A. et al., "A Theory for Phase Locking of Respiration in Cats to a Mechanical Ventilator," *American Journal of Physiology*, 246: R311-320, 1984.
Poon, C.S. et al., "Negative-Impedance Ventilation and Pressure Support Ventilation: A Comparative Study," *Respiratory Physiology*, 108: 117-127, 1997.
Poon, C.S. et al., "Plasticity of Cardio-Respiratory Neural Processing: Classification and Computational Functions," *Respiratory Physiology*, 122: 83-109, 2000.
Poon, C.S., "Organization of Central Pathways Mediating the Hering-Breuer Reflex and Carotid Chemoreflex," *Advances in Experimental Medicine and Biology*, 551: 95-100, 2004.
Poon, C.S. et al., "Nonassociative Learning as Gated Neural Integrator and Differentiator in Stimulus-Response Pathways," *Behavioral Brain Function*, 2: 29, 2006.
Poon, C. S. et al., "High-Pass Filtering of Carotid-Vagal Influences on Expiration in Rat: Role of N-methyl-D-aspartate Receptors," *Neuroscience Letters*, 284: 5-8, 2000.
Poon, C.S., "Control of Exercise Hyperpnoea During Assisted Breathing," Ph.D. thesis, UCLA School of Engineering, 1981.
Saito, Y. et al., "Apneustic Breathing in Children with Brainstem Damage Due to Hypoxic-Ischemic Encephalopathy," *Developmental Medicine and Child Neurology*, 41: 560-567, 1999.
Sharshar, T. et al., "Transdiaphragmatic Pressure Control of Airway Pressure Support in Healthy Subjects," *American Journal of Respiratory and Critical Care Medicine*, 168: 760-769, 2003.
Sinderby, C. et al., "Neural Control of Mechanical Ventilation in Respiratory Failure," *Nature Medicine*, 5: 1433-1436, 1999.
Simon, P.M. et al., "Entrainment of Respiration in Humans by Periodic Lung Inflations. Effect of State and CO(2)," *American Journal of Respiratory and Critical Care Medicine*, 160: 950-960, 1999.
Simon, P.M. et al., "Vagal Feedback in the Entrainment of Respiration to Mechanical Ventilation in Sleeping Humans," *Journal of Applied Physiology*, 89: 760-769, 2000.
Siniaia, M.S. et al., "Habituation and Desensitization of the Hering-Breuer Reflex in Rat," *Journal of Physiology 523 Pt 2*: 479-491, 2000.
Song, G. et al., "Functional and Structural Models of Pontine Modulation of Mechanoreceptor and Chemoreceptor Reflexes," *Respiratory Physiology and Neurobiology*, 143: 281-292, 2004.
Song, Y. et al., "Cytoarchitecture of Pneumotaxic Integration of Respiratory and Nonrespiratory Information in the Rat," *Journal of Neuroscience*, 26: 300-310, 2006.
Stanley, N.N. et al., "Changes in Strength of Lung Inflation Reflex During Prolonged Inflation," *Journal of Applied Physiology*, 38: 474-480, 1975.
Thille, A.W. et al., "Patient-Ventilator Asynchrony During Assisted Mechanical Ventilation," *Intensive Care Medicine*, 32: 1515-1522, 2006.
Tobin, M.J. et al., "Fighting the Ventilator," *Principles and Practice of Mechanical Ventilation*, pp. 1121-1136, McGraw-Hill, 2006.
Tobin, M. J. et al., *Principles and Practice of Mechanical Ventilation*, pp. 1185-1120, McGraw-Hill 2006.

(56) References Cited

OTHER PUBLICATIONS

Tobin, M.J. et al., "Patient-Ventilator Interaction," *American Journal Respiratory and Critical Care Medicine*, 163: 1059-1063, 2001.

Tobin, M.J., "Advances in Mechanical Ventilation," *New England Journal of Medicine*, 344: 1986-1996, 2001.

Tryfon, S. et al., "Hering-Breuer Reflex in Normal Adults and in Patients with Chronic Obstructive Pulmonary Disease and Interstitial Fibrosis," *Respiration*, 68: 140-144, 2001.

Vibert, J.F. et al., "Respiratory Oscillator Entrainment by Periodic Vagal Afferentes: An Experimental Test of a Model," *Biological Cybernetic*, 41: 119-130, 1981.

Widdicombe, J.G., "Respiratory Reflexes in Man and Other Mammalian Species," *Clinical Science*, 21: 163-170, 1961.

Younes, M. et al., "Central Adaptation to Inspiratory-Inhibiting Expiratory-Prolonging Vagal Input," *Journal of Applied Physiology*, 59: 1072-1084, 1985.

Younes, M. et al., "Temporal Changes in Effectiveness of an Inspiratory Inhibitory Electrical Pontine Stimulus," *Journal of Applied Physiology*, 62: 1502-1512, 1987.

Young, D. L. et al., "Integration-Differentiation and Gating of Carotid Afferent Traffic that Shapes the Respiratory Pattern," *Journal of Applied Physiology*, 94: 1213-1229, 2003.

Younes, M. et al., "A Method for Monitoring and Improving Patient: Ventilator Interaction," *Intensive Care Med*, 33: 1337-1346, 2007.

Ardaugh, B., "Under Pressure: Patients on Ventilators May Soon Breathe Easier," On-line at: http://owl.english.purdue.edu/media/pdf/20080924100215_732.pdf.

\* cited by examiner

MECHANICAL VENTILATOR

RELATED APPLICATION(S)

This application claims the benefit of U.S. Provisional Application No. 61/025,044, filed on Jan. 31, 2008.

The entire teachings of the above application(s) are incorporated herein by reference.

GOVERNMENT SUPPORT

The invention was supported, in whole or in part, by grants HL067966 (MIT OSP project number 6897891), HL079501 (MIT OSP project number 6898426), and HL072849 (MIT OSP project number 6896458) from the National Institute of Health. The Government has certain rights in the invention.

BACKGROUND OF THE INVENTION

Patient-ventilator synchrony is a major concern in critical care and is influenced by phasic lung-volume feedback control of the respiratory rhythm. Routine clinical application of positive end-expiratory pressure (PEEP) introduces a tonic input which, if unopposed, might disrupt respiratory-ventilator entrainment through sustained activation of the vagally-mediated Hering-Breuer reflex.

Mechanically ventilated patients in critical care who are unable to entrain their respiratory activity to the ventilator rhythm and who instead fight the ventilator often require sedation or even paralysis in order to avoid lung injury and improve pulmonary ventilation (M. J. Tobin, C. Alex, and P. J. Fahey "Fighting the ventilator," Principles and Practice of Mechanical Ventilation, pp. 1121-1136, McGraw-Hill, 2006). Patient-ventilator interaction is a complex process that is determined not only by the clinician-prescribed ventilator settings but also the patient's moment-to-moment reaction to the ventilator-delivered breath (C. R. Dick and C. S. Sassoon, "Patient-ventilator interactions," Clinical Chest Medicine 17: 423-438, 1996; E. Kondili, G. Prinianakis, and D. Georgopoulos, "Patient-ventilator interaction," British Journal of Anesthesia, 91: 106-119, 2003; M. J. Tobin, A. Jubran, and f. Laghi, "Patient-ventilator interaction," American Journal Respiratory and Critical Care Medicine, 163: 1059-1063, 2001; M. J. Tobin, "Advances in mechanical ventilation," New England Journal of Medicine, 344: 1986-1996, 2001). Although synchrony may be improved with the use of various patient-triggered ventilatory assist modes (C. S. Poon, H. H. Lebowitz, D. A. Sidney, and S. X. Li, "Negative-impedance ventilation and pressure support ventilation: a comparative study," Respiratory Physiology, 108: 117-127, 1997; C. Sinderby, P. Navalesi, J. Beck, Y. Skrobik, and N. Comtois, et al., "Neural control of mechanical ventilation in respiratory failure," Nature Medicine, 5: 1433-1436, 1999; T. Sharshar, G. Desmarais, B. Louis, G. Macadou, and R. Porcher, et al., "Transdiaphragmatic pressure control of airway pressure support in healthy subjects," American Journal of Respiratory and Critical Care Medicine, 168: 760-769, 2003) the latter are relatively complex, costly, and not always feasible or beneficial especially in neonates (M. W. Beresford, N. J. Shaw, and D. Manning "Randomized controlled trial of patient triggered and conventional fast rate ventilation in neonatal respiratory distress syndrome," Archive of Disease in Childhood Fetal Neonatal, Edition 82: F14-18, 2000; J. H. Baumer, "International randomized controlled trial of patient triggered ventilation in neonatal respiratory distress syndrome," Archive of Disease in Childhood Fetal Neonatal, Edition 82: F5-F10, 2000) or during prolonged mechanical ventilation (A. W Thille, P. Rodriguez, B. Cabello, F. Lellouche, and L. Brochard, "Patient-ventilator asynchrony during assisted mechanical ventilation," Intensive Care Medicine, 32: 1515-1522, 2006; D. C. Chao, D. J. Scheinhorn, and M. Stearn-Hassenpflug, "Patient-ventilator trigger asynchrony in prolonged mechanical ventilation," Chest, 112: 1592-1599, 1997), and may be prone to auto-triggering (H. Imanaka, M. Nishimura, M. Takeuchi, W. R. Kimball, and N. Yahagi, et al., "Auto triggering caused by cardiogenic oscillation during flow-triggered mechanical ventilation," Critical Care Medicine, 28: 402-407, 2000). Further complicating this process is the inevitable presence of extrinsic and/or intrinsic (auto) positive end-expiratory pressure (PEEP) (M. Oddo, F. Feihi, M. D. Schaller, and C. Perret, "Management of mechanical ventilation in acute severe asthma: practical aspects," intensive Care Medicine, 32: 501-510, 2006; P. E Pepe, and J. J Marini, "Occult positive end-expiratory pressure in mechanically ventilated patients with airflow obstruction: the auto-PEEP effect," American Review of Respiratory Disease, 126: 166-170, 1982; L. Brochard, "Intrinsic (or auto-) PEEP during controlled mechanical ventilation," Intensive Care Medicine, 28: 1376-1378, 2002), which may significantly influence the spontaneous breathing pattern (C. Haberthur, and J. Guttmann, "Short-term effects of positive end-expiratory pressure on breathing pattern: an interventional study in adult intensive care patients," Critical Care, 9: R407-415, 2005) and hence, patient-ventilator synchrony.

The rising popularity of patient-triggered assisted ventilation is premised on the general belief that patient-ventilator synchrony is difficult if not impossible with controlled (non-patient triggered) mechanical ventilation. On the contrary, many studies in anesthetized animals or awake or sleeping humans have shown that periodic lung inflation during controlled mechanical ventilation may entrain the respiratory rhythm to the ventilation frequency or some sub-harmonics close to the intrinsic respiratory frequency (G. A. Petrillo, L. Glass, and T. Trippenbach, "Phase locking of the respiratory rhythm in cats to a mechanical ventilator," Canadian Journal of Physiology and Pharmacology, 61: 599-607, 1983; C. Graves, L. Glass, D. Laporta, R. Meloche, and A. Grassino, "Respiratory phase locking during mechanical ventilation in anesthetized human subjects," American Journal of Physiology, 250: R902-909, 1986; S. Muzzin, P Baconnier, and G Benchetrit, "Entrainment of respiratory rhythm by periodic lung inflation: effect of airflow rate and duration," American Journal of Physiology, 263: R292-300, 1992; P. M. Simon, A. S. Zurob, W. M. Wies, J. C. Leiter, and R. D. Hubmayr, "Entrainment of respiration in humans by periodic lung inflations. Effect of state and CO(2)," American Journal of Respiratory and Critical Care Medicine, 160: 950-960, 1999; P. M. Simon, A. M. Habel, J. A. Daubenspeck, and J. C. Leiter, "Vagal feedback in the entrainment of respiration to mechanical ventilation in sleeping humans," Journal of Applied Physiology, 89: 760-769, 2000; P. F. Baconnier, G. Benchetrit, P. Pachot, and J. Demongeot, "Entrainment of the respiratory rhythm: a new approach," Journal of Theoretical Biology, 164: 149-162, 1993). The ratio of the respiratory frequency and ventilation frequency, termed the rotation number, is a measure of the relative strength of the entrainment, where the strongest ratio is 1:1 (P. F. Baconnier, G. Benchetrit, P. Pachot, and J. Demongeot, "Entrainment of the respiratory rhythm: a new approach," Journal of Theoretical Biology, 164: 149-162, 1993; J. F. Vibert, D. Caille, and J. P. Segundo, "Respiratory oscillator entrainment by periodic vagal afferentes: an experimental test of a model," Biological Cybernetic, 41: 19-130, 1981; G. A. Petrillo, and L. Glass, "A theory for phase locking of respiration in cats to a mechanical ventilator,"

American Journal of Physiology, 246: R311-320, 1984; M. Matsugu, J. Duffin, and C. S. Poon, "Entrainment, instability, quasi-periodicity, and chaos in a compound neural oscillator," Journal of Computational Neuroscience, 5: 35-51, 1998). In anesthetized animals such entrainment is abolished after bilateral vagotomy (J. F. Vibert, D. Caille, and J. P. Segundo, "Respiratory oscillator entrainment by periodic vagal afferentes: an experimental test of a model," Biological Cybernetic, 41: 119-130, 1981; G. A. Petrillo, and L. Glass, "A theory for phase locking of respiration in cats to a mechanical ventilator," American Journal of Physiology, 246: R311-320, 1984) and impaired after vagal cooling (S. Muzzin, T. Trippenbach, P. Baconnier, and G. Benchetrit, "Entrainment of the respiratory rhythm by periodic lung inflation during vagal cooling," Respiratory Physiology, 75: 157-172, 1998) indicating that it is mediated primarily by pulmonary slowly adapting stretch receptors and secondarily by pulmonary rapidly adapting receptors and/or vagal C-fibers.

SUMMARY OF THE INVENTION

Patient-ventilator synchrony is a major concern in critical care and is influenced by phasic lung-volume feedback control of the respiratory rhythm. Patient-ventilator interaction is a complex process that is determined not only by the clinician-prescribed ventilator settings but also the patient's moment-to-moment reaction to the ventilator-delivered breath.

A new mode of mechanical ventilation may provide a cost-effective solution to the problem of patient-venitilator synchrony.

The patient ventilator may employ a pressure generating mechanism to move breathable air into and out of a patient's respiratory system at a ventilator driven frequency. Additionally, the ventilator may employ a sensor to sense the patient's respiration. A control mechanism may automatically adjust the ventilator driven frequency of the pressure generating mechanism to the patient's respiration.

The frequency control mechanism may enforce an initial frequency on the pressure generating mechanism and adjust the frequency of the pressure generating mechanism responsive to a phase difference. The phase difference may indicate a difference between the frequency of the pressure generating mechanism and the patient's spontaneous respiratory frequency.

The control mechanism may approximate the patient's spontaneous respiratory frequency and tidal volume.

The control mechanism may automatically adjust the frequency of the pressure generating mechanism through closed-loop control. The control mechanism may adjust the frequency of the pressure generating mechanism until the difference between the frequency of the pressure generating mechanism and the patient's spontaneous respiratory frequency is within a preset limit. The control mechanism may automatically adjust the frequency of the pressure generating mechanism to the patient's respiratory frequency without requiring any external triggering device.

The mechanical ventilator may employ a ventilation pump that may operate at a frequency to cause a patient's respiration to entrain to the frequency. The mechanical ventilator may also employ a control mechanism to reduce phase difference between the ventilation pump operation and the patient's respiration.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

DETAILED DESCRIPTION OF THE INVENTION

Figure 1A:
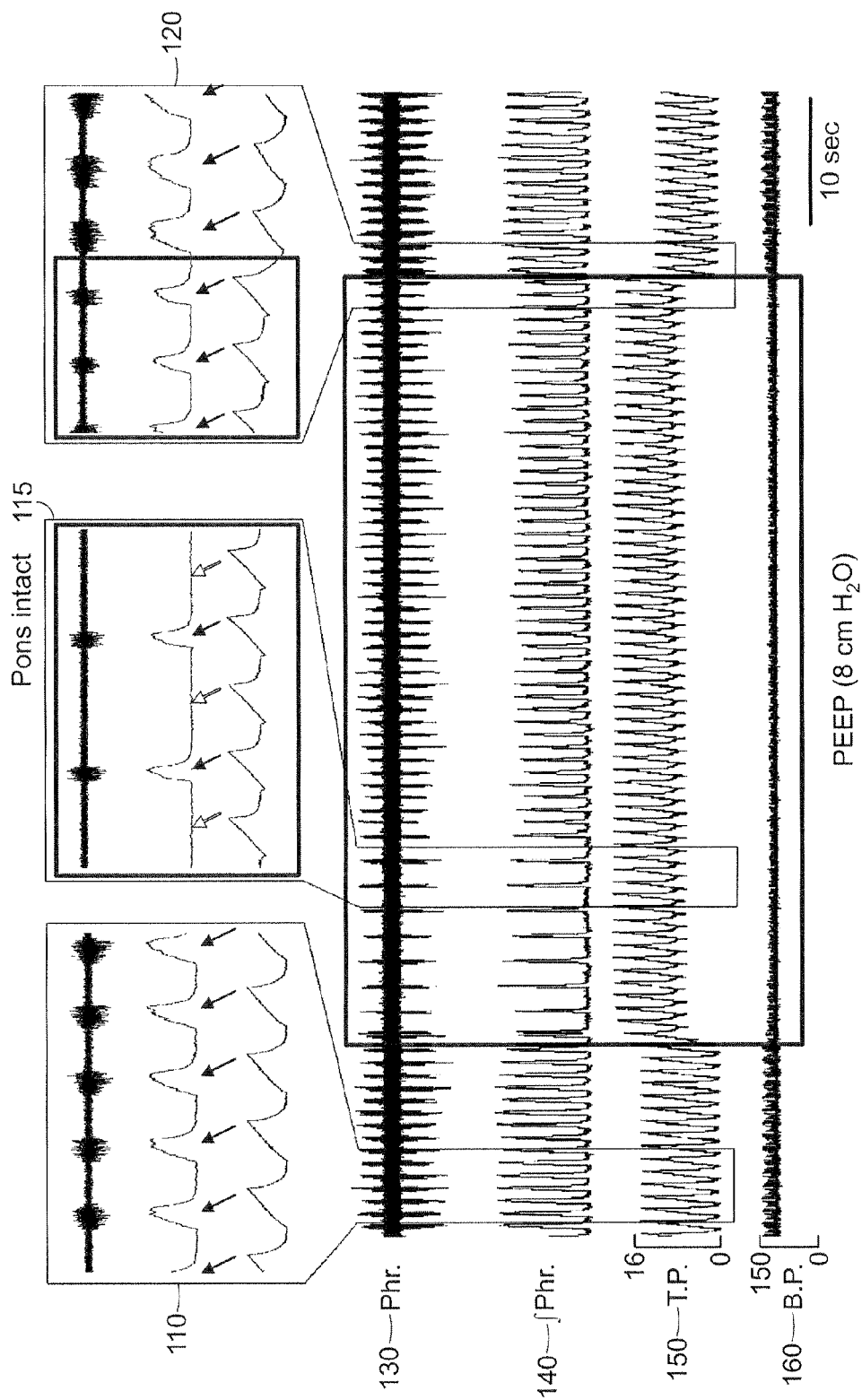
FIGS. 1a-1c demonstrates adaptations of respiratory-ventilator entrainment to positive end-expiratory pressure (PEEP) before and after pontine lesions in one rat with intact vagus nerves.

A description of example embodiments of the invention follows.

As described in (S. M. MacDonald, G. Song, C. S. Poon, "Nonassociative learning promotes respiratory entrainment to mechanical ventilation", PLoS ONE 2(9): e865. doi: 10.1371/journal.pone.0000865, Sep. 12, 2007), the teachings of which are incorporated by reference in its entirety, current methods of mechanical ventilator in critical care fall in two general categories: controlled (conventional) and assisted mechanical ventilation. In controlled mechanical ventilation, the ventilator settings such as frequency, tidal volume and ratio of inspiratory or expiratory durations are prescribed by the clinician and are non-adaptive to the patient's needs. This ventilation approach may sometimes lead to patient "fighting" the ventilator and may necessitate patient sedation or even paralysis. In assisted mechanical ventilation, the patient triggers the ventilator to deliver pressure-support or proportional (resistive and/or elastic) assist. It is generally believed that assisted ventilation allow better patient-ventilator synchrony and are more amenable to weaning patient off ventilators. However, patient-triggered assisted ventilators are more complicated and more costly, and may not be effective in neonates or in prolonged mechanical ventilation, and may be prone to auto-triggering. Some recent assist-mode ventilators have gone so far as using trans-diaphragmatic pressure or diaphragmatic EMG recordings in order to trigger the ventilator. These invasive measurements further complicate the clinical management and cost of mechanical ventilation.

The effects of extrinsic and intrinsic positive end-expiratory pressure (PEEP) on respiratory-ventilator entrainment during controlled mechanical ventilation are not very clear. If such entrainment is indeed mediated by phasic vagal volume input as predicted by theory (J. F. Vibert, D. Caille, and J. P. Segundo, "Respiratory oscillator entrainment by periodic vagal afferentes: an experimental test of a model," Biological Cybernetic, 41: 119-130, 1981; G. A. Petrillo, and L. Glass, "A theory for phase locking of respiration in cats to a mechanical ventilator," American Journal of Physiology, 246: R311-320, 1984), then sustained elevation of lung volume during PEEP may disrupt entrainment by activating the classic Hering-Breuer inflation reflex, which is one of the earliest demonstrated long-loop physiological feedback regulation mechanisms in mammals (E. Hering, "Self-steering of respiration through the nerves vagus," Breathing: Hering-Breuer Centenary Symposium London: Churchill, pp. 359-364, 1970; J. Breuer, "Self-steering of respiration through the nerves vagus," Breathing: Hering-Breuer Centenary Symposium London: Churchill, pp. 365-394, 1970). However, previous studies in anesthetized animals have shown that the Hering-Breuer reflex response to sustained lung inflation or vagal stimulation is not static but exhibits time-dependent nonchemically-mediated central adaptation (N. N. Stanley, M. D. Altose, N. S. Cherniack, and A. P. Fishman, "Changes in strength of lung inflation reflex during prolonged inflation," Journal of Applied Physiology, 38: 474-480, 1975; M. A. Grippi, A. I. Pack, R. O. Davies, and A. P. Fishman, "Adaptation to reflex effects of prolonged lung inflation," Journal of Applied Physiology, 58: 1360-1371, 1985; I. Yotnes, and J. Polacheck, "Central adaptation to inspiratory-inhibiting expiratory-prolonging vagal input," Journal of Applied Physiology, 59: 1072-1084, 1985; M. S. Siniaia, D. L. Young, and C. S. Poon CS, "Habituation and desensitization of the Hering-Breuer reflex in rat," Journal of Physiology 523 Pt 2: 479-491, 2000). Recent studies have ascribed such central adaptation to distinct forms of nonassociative learning (i.e., activity-dependent up- or down-regulation of the response to a continuous or repetitive stimulus) acting in concert: namely habituation via the nucleus tractus solitarius in dorsal medulla, and a novel form of nonassociative learning called desensitization via the classic pneumotaxic center in the dorsolateral pons (M. S. Siniaia, D. L. Young, and C. S. Poon CS, "Habituation and desensitization of the Hering-Breuer reflex in rat," Journal of Physiology 523 Pt 2: 479-491, 2000; C. S. Poon, and M. S. Siniaia, "Plasticity of cardio-respiratory neural processing: classification and computational functions," Respiratory Physiology, 122: 83-109, 2000; C. S. Poon, "Organization of central pathways mediating the Hering-Breuer reflex and carotid chemoreflex," Advances in Experimental Medicine and Biology, 551: 95-100, 2004; G. Song, and C. S. Poon, "Functional and structural models of pontine modulation of mechanoreceptor and chemoreceptor reflexes," Respiratory Physiology and Neurobiology, 143: 281-292, 2004).

Desensitization (converse of secondary sensitization) is distinguished from habituation (converse of primary sensitization) by the explicit expression of memory rebound and recovery effects in the post-stimulation response (C. S. Poon, and D. L. Young, "Nonassociative learning as gated neural integrator and differentiator in stimulus-response pathways. Behavioral Brain Function 2: 19, 2006). In the rat, desensitization of the vagally-induced Hering-Breuer reflex is abolished by lesioning the pneumotaxic center or systemic administration of the noncompetitive NMDA receptor antagonist MK-801 (M. S. Siniaia, D. L. Young, and C. S. Poon CS, "Habituation and desensitization of the Hering-Breuer reflex in rat," Journal of Physiology 523 Pt 2: 479-491, 2000; C. S. Poon, D. L. Young, and M. S. Siniaia, "High-pass filtering of carotid-vagal influences on expiration in rat: role of N-methyl-D-aspartate receptors," Neuroscience Letters 284: 5-8, 2000). Habituation and desensitization have been likened to monophasic or biphasic neural differentiators, without or with memory rebound, or high-pass filters which selectively suppress tonic inputs in favor of phasic inputs (C. S. Poon, and M. S. Siniaia, "Plasticity of cardio-respiratory neural processing: classification and computational functions," Respiratory Physiology, 122: 83-109, 2000; C. S. Poon, and D. L. Young, "Nonassociative learning as gated neural integrator and differentiator in stimulus-response pathways. Behavioral Brain Function 2: 29, 2006; C. S. Poon, D. L. Young, and M. S. Siniaia, "High-pass filtering of carotid-vagal influences on expiration in rat: role of N-methyl-D-aspartate receptors," Neuroscience Letters 284: 5-8, 2000; D. L. Young, F. L. Eldridge, C. S. Poon, "Integration-differentiation and gating of carotid afferent traffic that shapes the respiratory pattern," Journal of Applied Physiology, 94: 1213-1229, 2003).

These recent revelations raise the intriguing possibility that vital physiological functions such as reflex modulation of the mammalian respiratory rhythm during controlled mechanical ventilation could be subject to nonassociative learning, a basic behavioral paradigm which has been widely studied in invertebrate animal models such as Aplysia or C. elegans and in certain cognitive functions such as the acoustic startle response in mammals (C. S. Poon, and D. L. Young, "Nonassociative learning as gated neural integrator and differentiator in stimulus-response pathways. Behavioral Brain Function 2: 29, 2006), but rarely in a routine clinical setting. However, although habituation and desensitization of the Hering-Breuer reflex have been demonstrated during electrical stimulation of vagal pulmonary afferent fibers in rats (M. S. Siniaia, D. L. Young, and C. S. Poon CS, "Habituation and desensitization of the Hering-Breuer reflex in rat," Journal of Physiology 523 Pt 2: 479-491, 2000), they have not been verified by direct lung inflation in these animals.

The present invention relates to demonstrating that pneumotaxic desensitization and extra-pontine habituation of the Hering-Breuer reflex are manifested during lung inflation in vagi-intact animals and indeed, play an important role in promoting respiratory-ventilator entrainment in the face of tonic vagal volume input during controlled mechanical ventilation under PEEP.

One embodiment of the invention relates to a new mode of mechanical ventilation that is based on patient-ventilator entrainment. Entrainment is a nonlinear dynamical phenomenon, coupled oscillators, that is of potential clinical significance in that it allows the spontaneous, barring voluntary, respiratory rhythm to synchronize with the ventilator naturally without any external triggering device necessary. The effect of entrainment has not been fully exploited in current assist/support-mode ventilators that rely on patient triggering. Entrainment has been robustly demonstrated in normal humans during wakefulness or non-REM sleep or under anesthesia, and to some extent in subjects after lung transplant suggesting that other respiratory-related afferents, such as those from the chest wall, may be recruited after vagotomy to maintain entrainment.

Entrainment may be disrupted by changes in positive end-expiratory pressure (PEEP) levels. Extrinsic PEEP is routinely used in respiratory failure as a means to keep the lungs distended, or during continuous positive-pressure ventilation to keep the upper airways patent. Additionally, intrinsic (i.e., auto) PEEP may result when the inspiratory or expiratory ratio is not properly adjusted or in patients with expiratory flow limitation such as chronic obstructive pulmonary disease or asthma. Changes in the PEEP level alter the patient's spontaneous respiratory rhythm as a result of the Hering-Breuer lung inflation reflex, and thus are potentially disruptive to patient-ventilator entrainment.

One aspect of the invention relates to the fact that patients are capable of counteracting the Hering-Breuer reflex through "nonassociative learning," i.e., habituation and desensitization, of the respiratory system (S. M. MacDonald, G. Song, and C. Poon, "Nonassociative learning Promotes Respiratory Entrainment to Mechanical Ventilation," PLoS ONE, 2(9): e865, 2007). This means that the patient's respiratory control system is intrinsically designed to entrain itself to a ventilator, an important revelation that has not been recognized in any present-day mechanical ventilators.

In one example embodiment of the present invention, an entrainment-based ventilator design calls for a mechanism to automatically adjust the ventilator frequency appropriate to the patient's breathing frequency. This adjustment is performed through closed-loop control. Typically, the entrained respiratory activity may precede or lag behind machine inflation depending on whether spontaneous respiratory frequency is higher or lower than the ventilator frequency. Therefore, suitable choice or closed-loop control of ventilator frequency to match the spontaneous respiratory frequency is crucial for optimal ventilatory unloading.

Unlike patient-triggered assisted ventilators, where the patient triggers the ventilator to deliver air pressure at a frequency that is directly responsive to the patient's and may be unsteady, the entrainment-based ventilator of this example embodiment determines the frequency without triggering from the patient and automatically adjusts the steady ventilator frequency appropriate to the patient's breathing frequency. Although, a medical practitioner may initially set the entrainment-based ventilator to operate at a set initial frequency, the ventilator will automatically adjust this ventilator-determined frequency to the breathing frequency of the patient. The ventilator will continue to cycle at its ventilator-driven frequency even if it does not receive a trigger from the patient.

Entrainment-based ventilators may also facilitate the process of weaning a patient from a ventilator, which is a major concern for ventilator-dependent patients (M. J. Tobin and Amal Jubran, "Principles and practice of mechanical ventilation," McGraw-Hill 2006, pp. 1185-1120).

Methods

All experimental protocols were reviewed and approved by the Massachusetts Institute of Technology Committee on Animal Care in accordance with published guidelines.

Animal Preparation

Experiments were performed on 17 urethane-anesthetized male Sprague-Dawley rats. The rats weighed approximately between 300 g to 350 g. The general procedures for animal surgery and anesthesia, mechanical ventilation and PEEP, cardiorespiratory, body temperature monitoring, and phrenic nerve recording, and etc. are described in (M. S. Siniaia, D. L. Young, and C. S. Poon CS, "Habituation and desensitization of the Hering-Breuer reflex in rat," Journal of Physiology 523 Pt 2: 479-491, 2000; G. Song, Y. Yu, C. S. Poon, "Cytoarchitecture of pneumotaxic integration of respiratory and nonrespiratory information in the rat. Journal of Neuroscience," 26: 300-310, 2006; McGuire M. S. M. Macdonald, G. Song, C. S. Poon, "Phrenic long-term facilitation is robust to hypercapnia and hypocapnia but not hyperventilatory hypotension under PEEP," Respiratory Physiology and Neurobiology, 158: 107-111, 2007).

Pontine Stimulation and Lesion

The pneumotaxic center in the rat dorsolateral pons is as defined in (G. Song, Y. Yu, C. S. Poon, "Cytoarchitecture of pneumotaxic integration of respiratory and non-respiratory information in the rat," Journal of Neuroscience, 26: 300-310, 2006). A tungsten electrode with shaft diameter 0.1 mm, tip 1-3μm, and impedance 8-11 MΩ was inserted stereotaxically into the dorsolateral pons, at 2.4-2.6 mm lateral from midline, −0.2-+0.2 mm from lambda level, and at depth of 7.5-8.5 mm from lambda surface. The latter was explored with electrical stimulation, at 100 Hz, pulse duration 0.3 ms, 30-40 μA, 10-15 sec, to determine the loci that produced the strongest respiratory inhibition. In some animals, 1-min long-train electrical stimulation (40 Hz) was delivered at those loci to test the respiratory responses before making lesions. Electrolytic lesions at such loci were made bilaterally by passing an anodal D.C. current (20-30 μA, for 30 sec). Subsequent electrical stimulation at the lesioned loci did not cause any respiratory response.

Histology

At the end of the experiment, the animal was killed with overdose of urethane (2 g/kg) and perfused with 0.05 M PBS and 4% paraformaldehyde. The brainstem was removed, post-fixed in 4% paraformaldehyde for 7 days, and cut into 80-μm sections with a vibratome. The actual loci of lesions were examined histologically. Data were discarded if the lesions were outside the dorsolateral pons.

Results

Figure 1B:
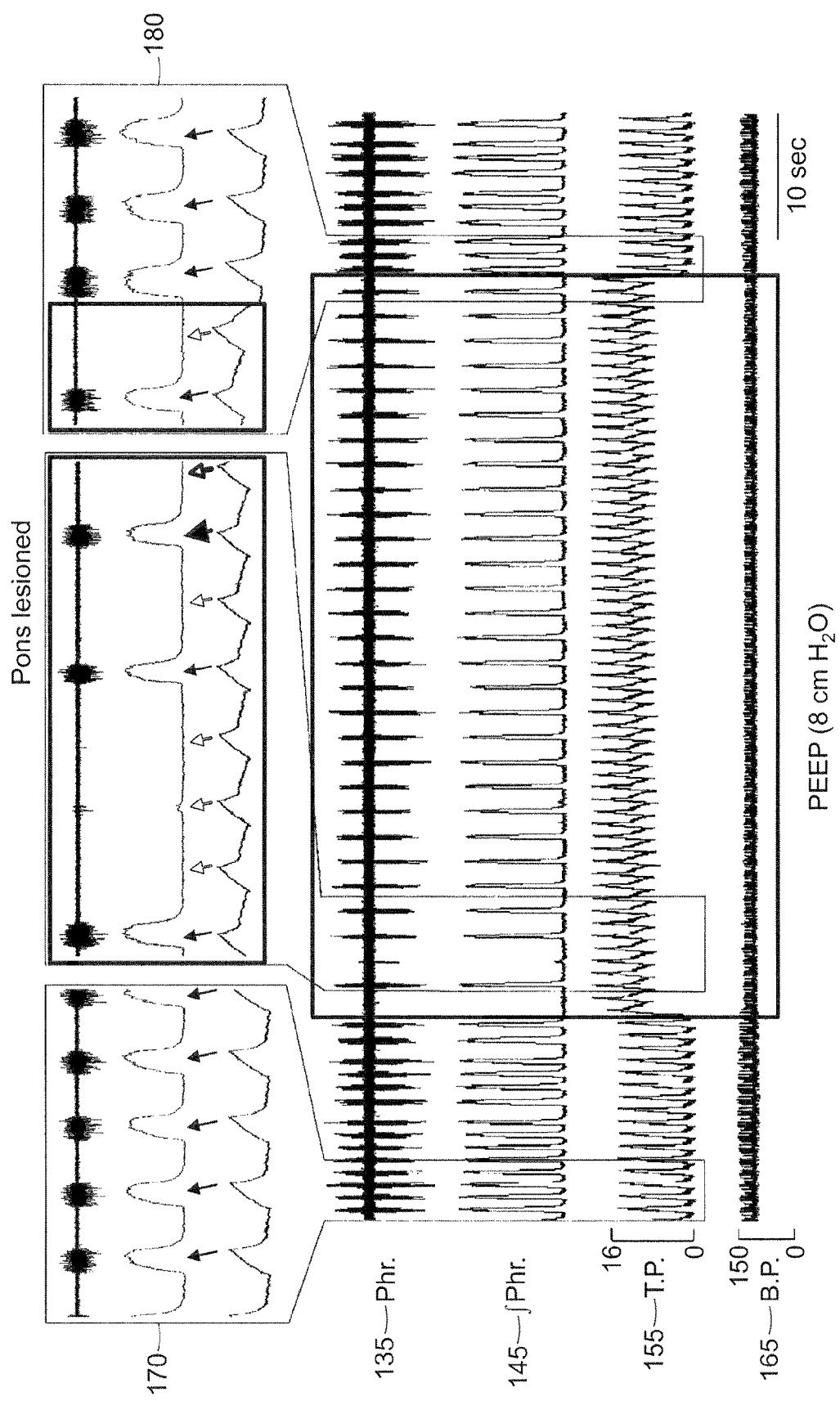

FIG. 1 illustrates the time-dependent adaptations of respiratory-ventilator entrainment to the abrupt on-off application of PEEP in a urethane-anesthetized, pancuronium-paralyzed animal with intact vagi, before (FIG. 1a) and after (FIG. 1b) bilateral pontine lesions. FIG. 1a demonstrates the case when in the absence of PEEP and with pons-intact, phrenic discharge was entrained at a ratio of 1:1 to the ventilator rhythm. Similar entrainment pattern was also observed before the animal was injected pancuronium. Close examination of the instantaneous tracheal pressure and phrenic discharge showed that they were phase-locked to one another, with phrenic activity beginning and ending slightly in advance of the onset 10 and offset 120 of inflation respectively. Insets 110, 120 demonstrate expanded views of selected breaths. In FIG. 1a, Phr 130 denotes phrenic nerve discharge, ∫Phr 140 denotes the integrated phernic signal, T.P. 150 denotes tracheal pressure (cm $H_2O$) at 60 cpm, and B.P. 160 denotes the arterial blood pressure (mm Hg).

Upon application of PEEP, as shown in inset 115, the entrainment to ratio was abruptly switched to 1:2. Phrenic activity remained phase-locked to the inflation phase every other ventilator cycle. This 1:2 entrainment lasted 5-30 seconds before abruptly reverting to a 1:1 ratio. This resulted in the onset of phrenic activity to lag behind inflation although the offset still occurred before the end of inflation (as shown in FIG. 1a, inset 120). Thus, the adverse effect of PEEP was "filtered" or "buffered" by respiratory adaptation although the phase relation of the entrainment was altered. PEEP also decreased the phrenic discharge duration and amplitude. Upon removal of the PEEP, the phrenic discharge immediately returned to the control level.

As shown in FIG. 1b, after pontine lesions, phrenic activity remained entrained at a ratio of 1:1 to the ventilator in this animal. Application of PEEP abruptly switched the entrainment to a ratio of 1:4 along with decreased phrenic discharge duration and amplitude. Thereafter, the entrainment improved to a ratio of 1:2 and remained so throughout the PEEP test. Upon removal of the PEEP, the entrainment promptly returned to corresponding pre-PEEP patterns. Also, after pontine lesions in this animal, phrenic activity showed a phase delay in its onset relative to that of inflation regardless of the presence or absence of PEEP (FIG. 1b, 170, 180). In FIG. 1b, Phr 135 denotes phrenic nerve discharge, ∫Phr 145 denotes the integrated phernic signal, T.P. 155 denotes tracheal pressure (cm $H_2O$) at 60 cpm, and B.P. 165 denotes the arterial blood pressure (mm Hg).

Figure 1C:
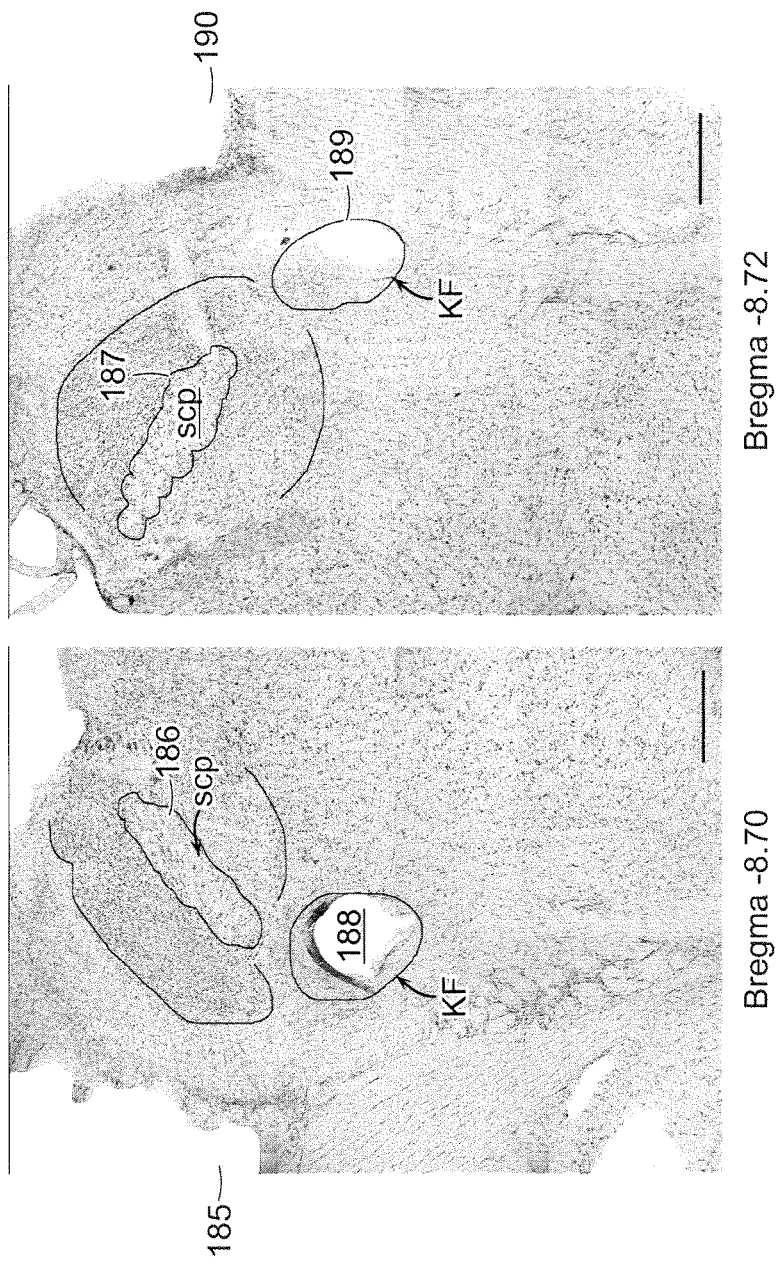

FIG. 1c shows the histological definition of lesions in the pneumotaxic center. Specifically, FIG. 1c demonstrates the extent of lesions covering almost the entire Kölliker-Fuse (KF 188, 189) nucleus 185, as well as the ventrolateral part of this nucleus 190. Areas marked as "scp" 186,187 mark the superior cerebellar peduncle.

Figure 2:
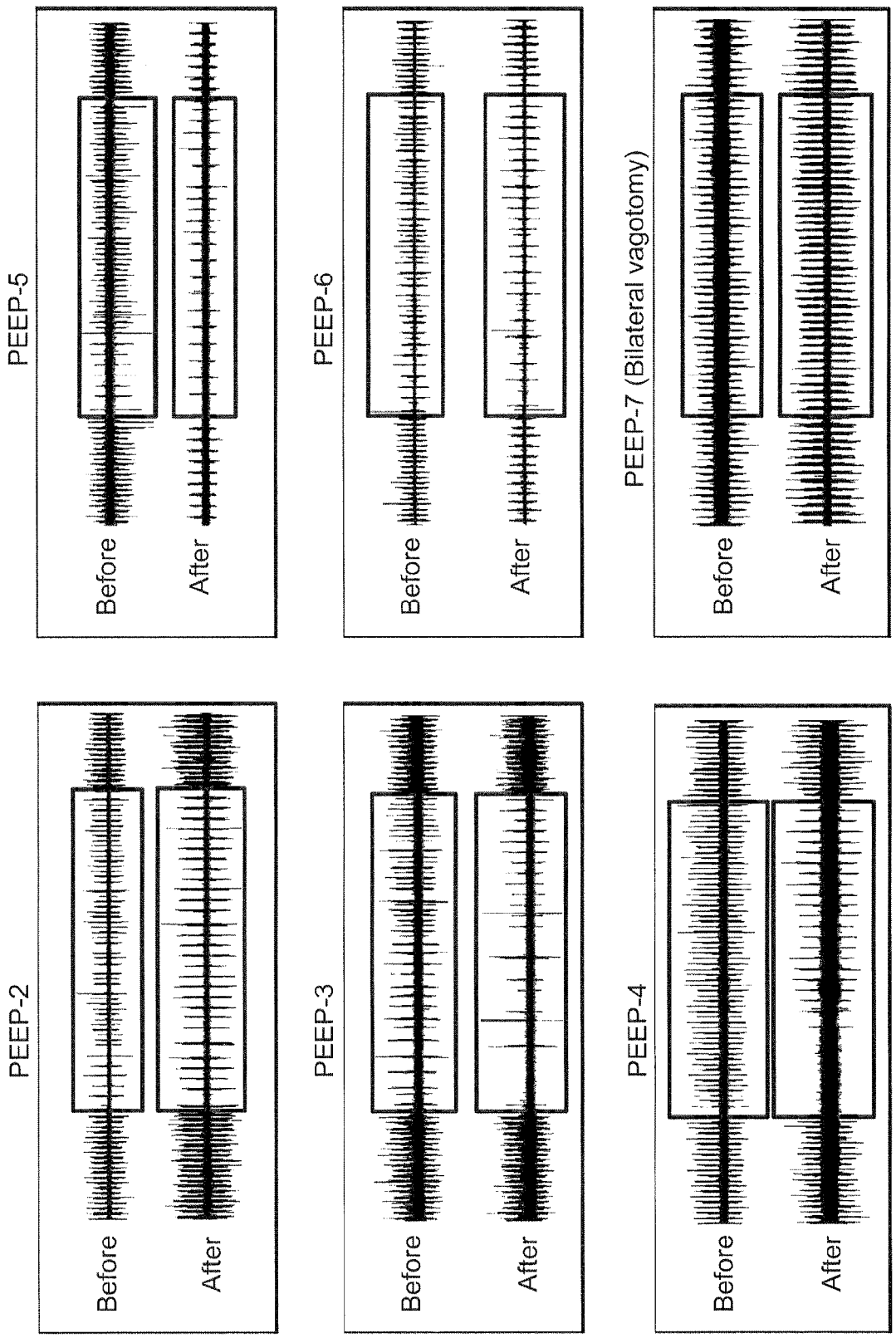
FIG. 2 demonstrates effects of (PEEP) before and after pontine lesions in five other rats with intact vagus nerves and one with vagus nerves cut.

FIG. 2 demonstrates observed effects of PEEP in five other animals before and after pontine lesions. In two vagi-intact animals (PEEP-5 and PEEP-6), respiratory-ventilator entrainment ratio became 1:2 after pontine lesions suggesting increased disparity between the spontaneous respiratory frequency and ventilator frequency. Upon application of PEEP the entrainment ratio switched to 1:4 or even higher ratios before adapting to a 1:3 pattern. In all animals, respiratory-ventilator entrainment and its adaptation to PEEP were impaired but not abolished after pontine lesions.

In a Vagotomized animal (PEEP-7), under bilateral vagotomy, respiratory-ventilator entrainment was abolished and no discernible changes in phrenic discharge were elicited by PEEP before or after pontine lesions. Results for five other vagotomized animals were similar (not shown here).

Figure 3A:
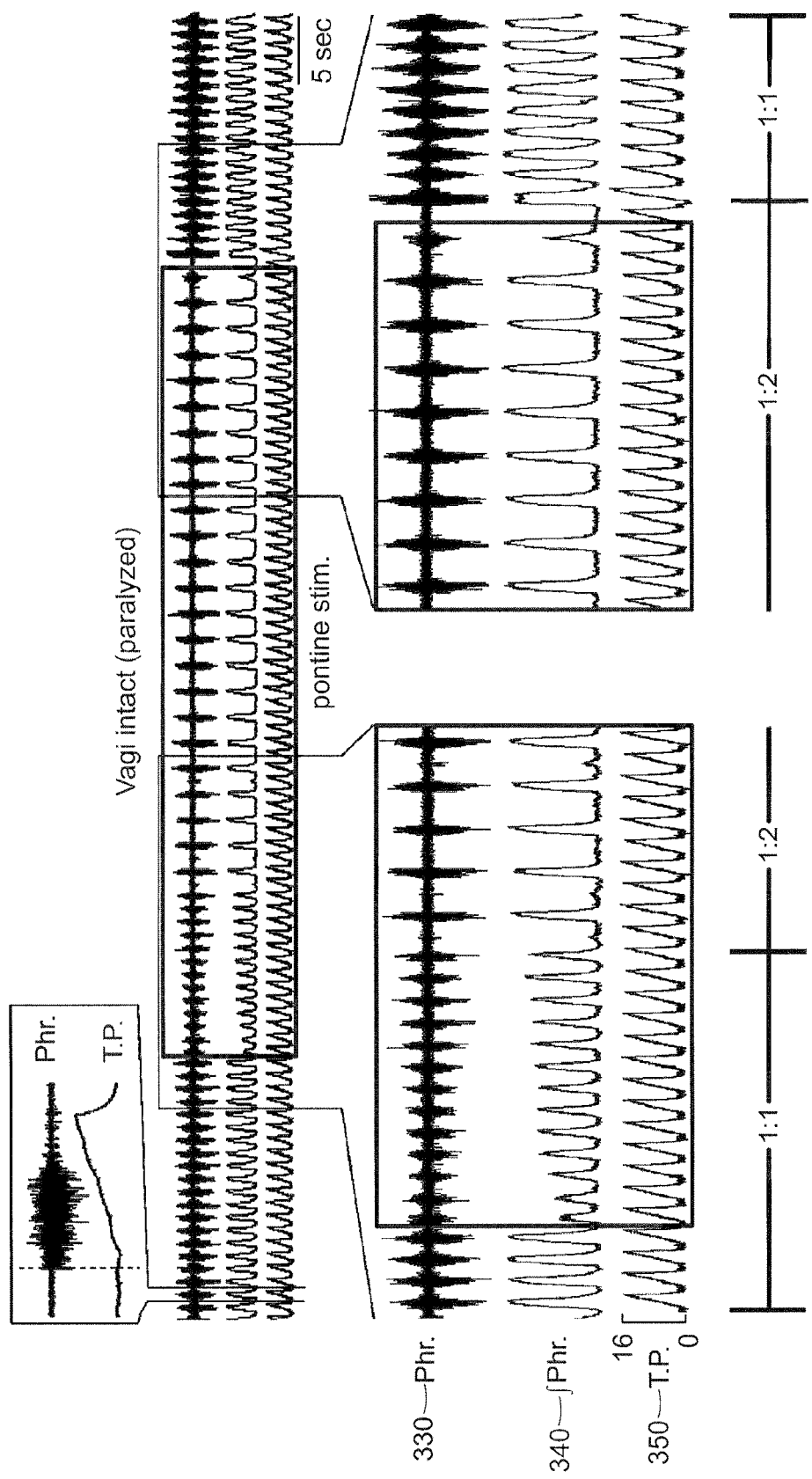
FIGS. 3a-3c demonstrates the disruption of respiratory-ventilator entrainment by unilateral stimulation at the dorsolateral pons.
Figure 3B:
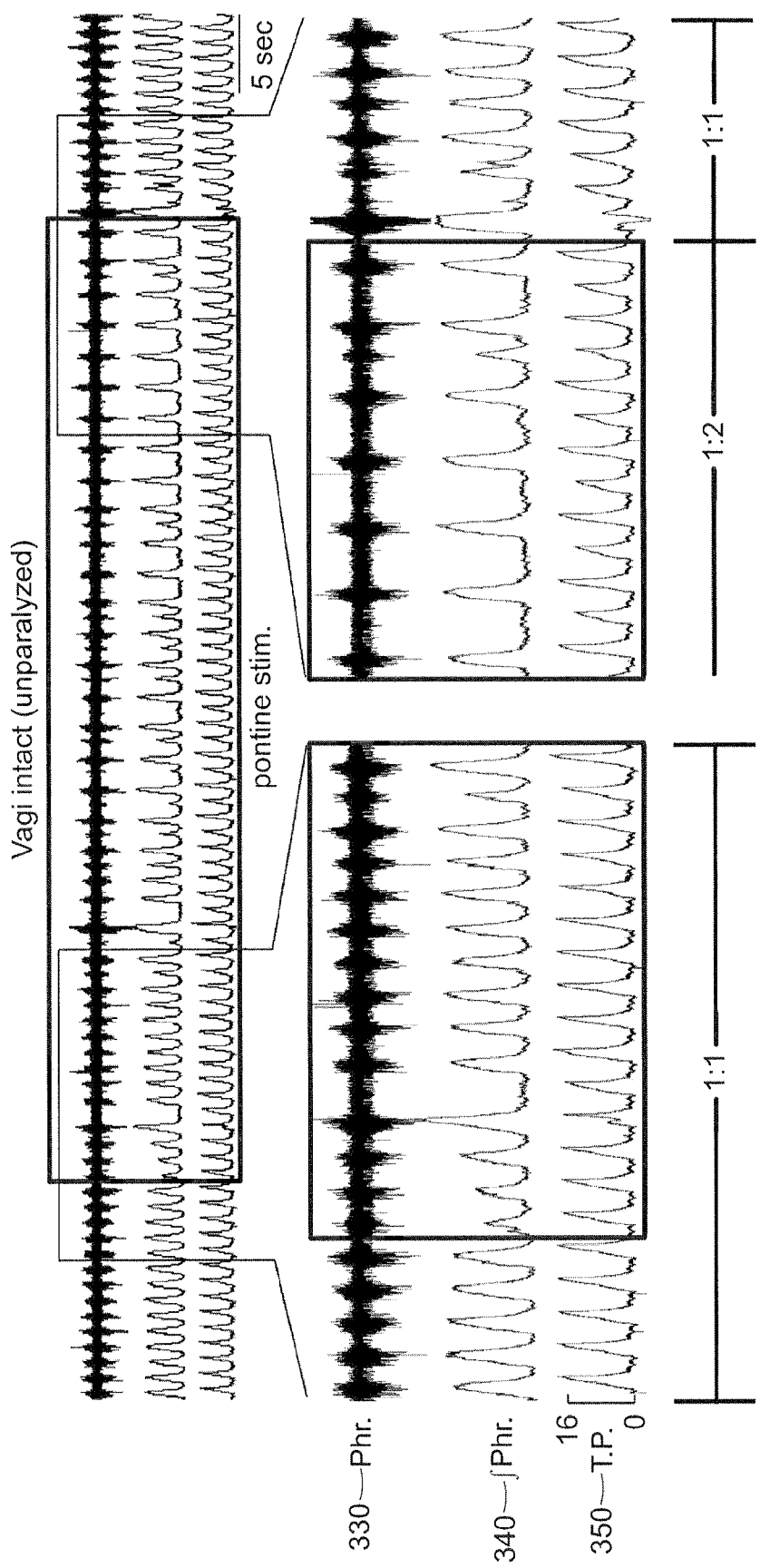
Figure 3C:
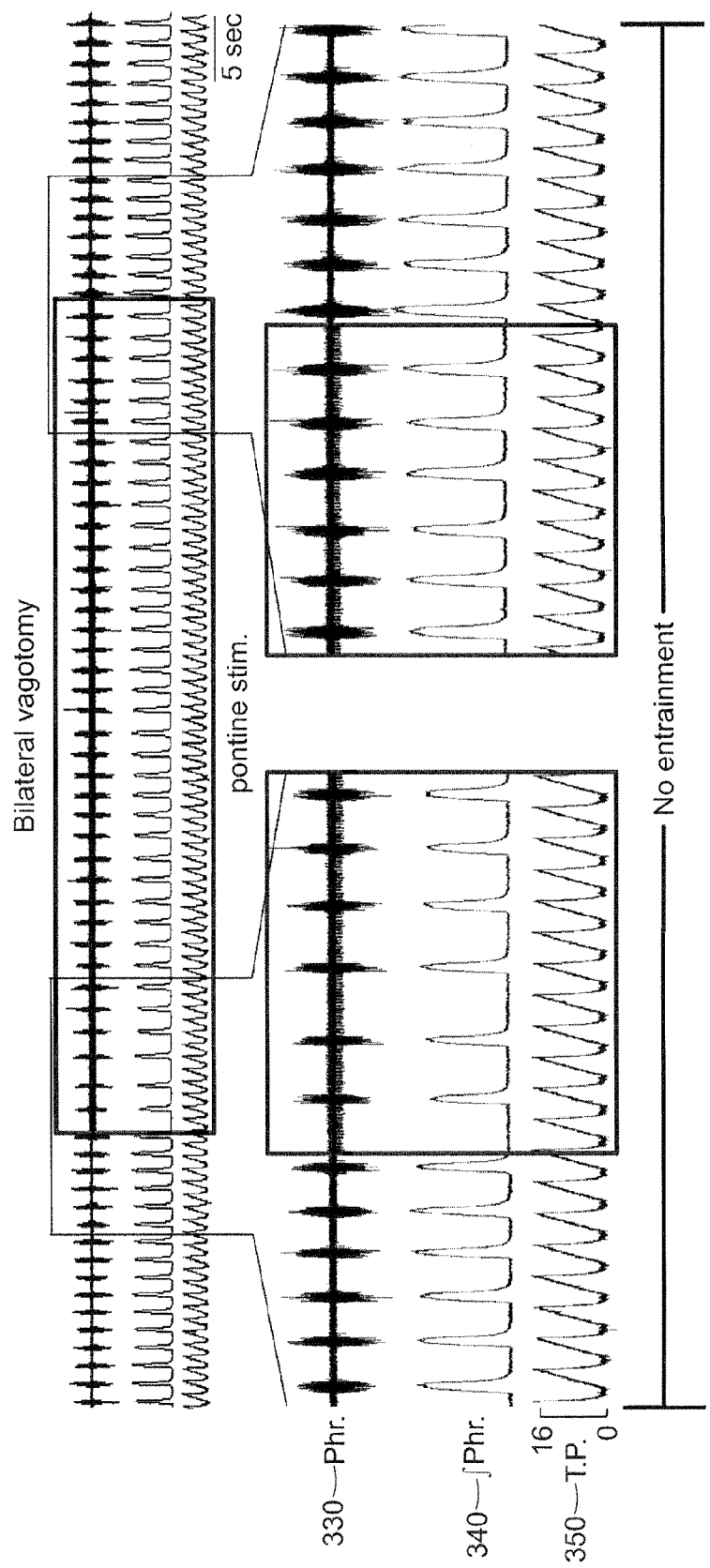

Adaptation of Respiratory-ventilator Entrainment to Unilateral Pontine Stimulation FIG. 3 demonstrates the disruption of respiratory-ventilator entrainment by unilateral stimulation at the dorsolateral pons. As shown in FIGS. 3a and 3B, in five vagi-intact animals, 4 paralyzed (FIG. 3a), 1 un-paralyzed (FIG. 3b), unilateral electrical stimulation at the dorsolateral pons initially decreased the amplitude of phrenic discharge by greater than 50% without affecting the respiratory entrainment. This initial inhibition lasted 15-20 seconds, during which the phrenic discharge gradually adapted toward the control amplitude. Thereafter, the entrainment ratio abruptly switched to 1:2. Upon cessation of stimulation, the entrainment ratio usually returned to 1:1 immediately but occasionally could take longer. In FIGS. 3a, 3b, 3c Phr 330 denotes phrenic nerve discharge, ∫Phr 340 denotes the integrated phernic signal, and T.P. 350 denotes tracheal pressure (cm $H_2O$) at 60 cpm. Thus, the response in the un-paralyzed animal was more variable but the overall effects were similar to those of the paralyzed animal.

FIG. 3c demonstrates the absence of respiratory-ventilator entrainment before, during or after pontine stimulation in the same animal shown in FIG. 3a after vagotomy. In a paralyzed animal after vagotomy, unilateral electrical stimulation at the dorsolateral pons elicited abrupt inhibition of phrenic discharge (but to a much lesser extent than when vagi were intact) and significant prolongation of expiratory duration, both effects adapting gradually as the stimulation continued as reported previously in vagotomized animals (M. Younes, J. Baker, J. E. Remmers, "Temporal changes in effectiveness of an inspiratory inhibitory electrical pontine stimulus," Journal of Applied Physiology, 62: 1502-1512, 1987). Entrainment was not observed before, during or after stimulation. Similar effects were seen in three other paralyzed animals after vagotomy (not shown).

Discussion

The results presented above confirm previous findings that controlled mechanical ventilation at a suitable frequency could entrain respiratory activity 1:1 in animals with intact vagi but not after vagotomy (J. F. Vibert, D. Caille, and J. P. Segundo, "Respiratory oscillator entrainment by periodic vagal afferentes: an experimental test of a model," Biological Cybernetic, 41: 119-130, 1981; G. A. Petrillo, and L. Glass, "A theory for phase locking of respiration in cats to a mechanical ventilator," American Journal of Physiology, 246: R311-320, 1984). The results also demonstrate that the application of PEEP momentarily dampened the entrainment but this adverse effect was gradually buffered by respiratory adaptation via nonassociative learning. Bilateral lesions of the dorsolateral pons weakened the respiratory adaptation to PEEP whereas sustained stimulation of the dorsolateral pons weakened the entrainment independent of PEEP. These findings corroborate the notion of pneumotaxic desensitization and extra-pontine habituation of the Hering-Breuer reflex previously demonstrated during vagal stimulation (M. S. Siniaia, D. L. Young, and C. S. Poon CS, "Habituation and desensitization of the Hering-Breuer reflex in rat," Journal of Physiology 523 Pt 2: 479-491, 2000), by showing that similar pontomedullary-mediated adaptations are also manifested during sustained lung inflation. Such central sites-specific habituation and desensitization of the Hering-Breuer reflex provide a useful experimental model of nonassociative learning in mammals that is of particular significance in understanding the mechanisms of respiratory rhythmogenesis and entrainment of coupled oscillators, and in the clinical management of mechanical ventilation in respiratory failure.

Respiratory-Ventilator Entrainment is Impaired by Tonic Vagal Volume Input

In anesthetized, vagi-intact animals after acid-induced lung injury, the application of PEEP promotes phasic respiratory activity during neurally-adjusted ventilatory assist (J. C. Allo, J. C. Beck, L. Brander, F. Brunet, and A. S. Slutsky, et al., "Influence of neurally adjusted ventilatory assist and positive end-expiratory pressure on breathing pattern in rabbits with acute lung injury," Critical Care Medicine, 34: 2997-3004, 2006). In those animals, the application of PEEP or vagotomy may be beneficial in restoring normal respiratory rhythm by precluding vagally-mediated lung deflation reflex secondary to the collapse of lung units following injury.

However, the results demonstrated above showed that in animals with normal lungs respiratory entrainment to mechanical ventilation was dampened by PEEP, most probably via corresponding activation of the Hering-Breuer inflation reflex and consequent slowing of the respiratory rhythm. This is indicated by the following observations: a) the decrease of entrainment during PEEP was transient and with a similar time course as the reported central adaptation of the Hering-Breuer reflex during sustained lung inflation (N. N. Stanley, M. D. Altose, N. S. Cherniack, and A. P. Fishman, "Changes in strength of lung inflation reflex during prolonged inflation," Journal of Applied Physiology, 38: 474-480, 1975; M. A. Grippi, A. I. Pack, R. O. Davies, and A. P. Fishman, "Adaptation to reflex effects of prolonged lung inflation," Journal of Applied Physiology, 58: 1360-1371, 1985); b) the impairment worsened after bilateral lesioning of the pneumotaxic center, a site known to mediate the desensitization component of the central adaptation of the Hering-Breuer inflation reflex (M. S. Siniaia, D. L. Young, and C. S. Poon CS, "Habituation and desensitization of the Hering-Breuer reflex in rat," Journal of Physiology 523 Pt 2: 479-491, 2000; C. S. Poon, "Organization of central pathways mediating the Hering-Breuer reflex and carotid chemoreflex," Advances in Experimental Medicine and Biology, 551: 95-100, 2004); c) electrical stimulation of the pneumotaxic region resulted in similar impairment of respiratory-ventilator entrainment as under PEEP, in agreement with previous finding that such stimulation elicits changes in the respiratory rhythm similar to the Hering-Breuer inflation reflex (M. Younes, J. Baker, J. E. Remmers, "Temporal changes in effectiveness of an inspiratory inhibitory electrical pontine stimulus." Journal of Applied Physiology, 62: 1502-1512, 1987); and d) bilateral vagotomy abolished respiratory-ventilator entrainment and corresponding influences of the pneumotaxic center and of PEEP. These observations taken together strongly support the notion that respiratory-ventilator entrainment is mediated by phasic vagal volume input and is impaired by tonic vagal volume input during PEEP due to sustained activation of the Hering-Breuer reflex.

Habituation and Desensitization of Hering-Breuer Reflex During PEEP

The results presented above shows that the acute adverse effect of PEEP is effectively negated by nonassociative learning acting as a high-pass filter or buffer for the tonic input. This is accomplished in part through desensitization of the pneumotaxic center, but also through extra-pontine mechanisms, such as habituation of the primary pathway for vagal lung volume input (M. S. Siniaia, D. L. Young, and C. S. Poon CS, "Habituation and desensitization of the Hering-Breuer reflex in rat," Journal of Physiology 523 Pt 2: 479-491, 2000; C. S. Poon, "Organization of central pathways mediating the Hering-Breuer reflex and carotid chemoreflex," Advances in Experimental Medicine and Biology, 551: 95-100, 2004) or other vagal afferent inputs (S. Muzzin, T. Trippenbach, P. Baconnier, and G. Benchetrit, "Entrainment of the respiratory rhythm by periodic lung inflation during vagal cooling," Respiratory Physiology, 75: 157-172, 1998), or adaptation of the lung stretch receptors themselves (N. N. Stanley, M. D. Altose, N. S. Cherniack, and A. P. Fishman, "Changes in strength of lung inflation reflex during prolonged inflation," Journal of Applied Physiology, 38: 474-480, 1975), which remained operative after pontine lesions. In this experimental setting the post-stimulation memory characteristic of pontine desensitization, which distinguishes the latter from vagal habituation, is not discernible because this effect contributes to the restoration instead of disruption of respiratory-ventilator entrainment upon the removal of PEEP. Nevertheless, the specific contribution of the pons to respiratory adaptation during PEEP is clearly seen in most pontine-lesioned animals (PEEP1-PEEP4), although in some animals (PEEP5 and PEEP6) the impairment of respiratory adaptation to PEEP after pontine lesions might also involve a general weakening of respiratory-ventilator entrainment due to increased disparity between the spontaneous respiratory rhythm and the ventilator frequency.

Figure 4A:
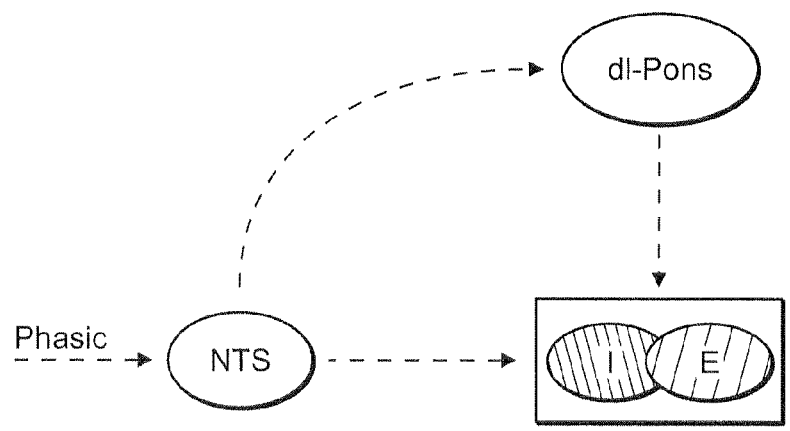
FIGS. 4a-4c demonstrates mechanisms of respiratory-ventilator entrainment and its buffering by differentiator-type nonassociative learning.
Figure 4B:
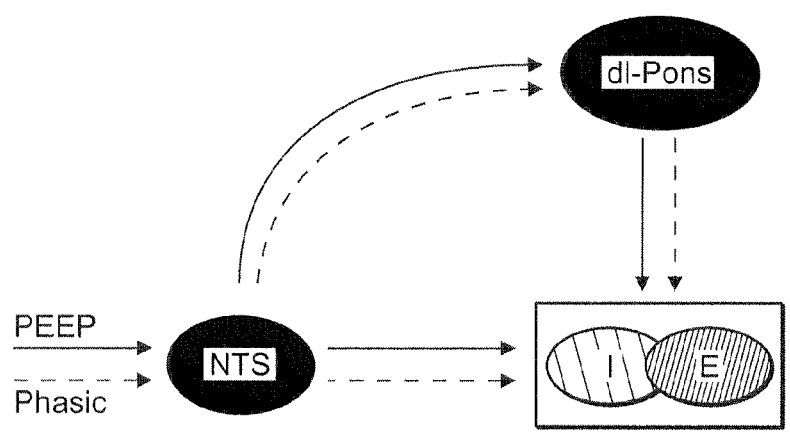
Figure 4C:
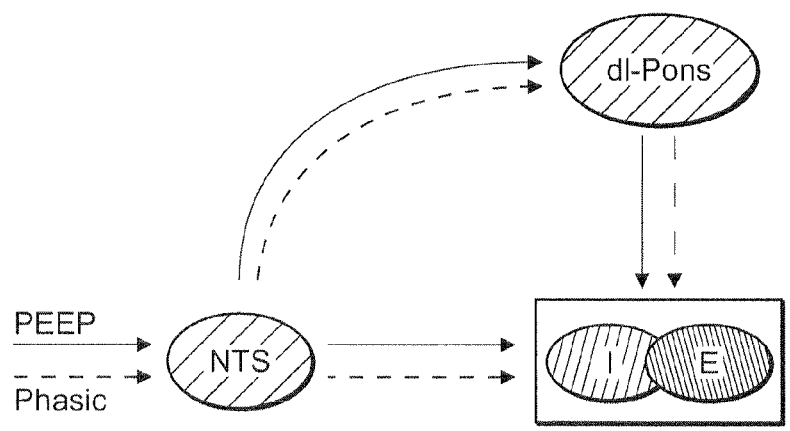

FIG. 4 illustrates the suggested pontomedullary mechanisms of respiratory-ventilator entrainment and nonassociative learning adaptation that are compatible with these findings. Note that the possible reciprocal connections for all paths are not shown. FIG. 4a demonstrates the case in the absence of PEEP. In this case the phasic volume-related inputs entrain the respiratory rhythm generator (I-E) via the nucleus tractus solitarius (NTS), which also modulates the pneumotaxic center in dorsolateral pons (dl-pons). As illustrated in FIG. 4b, immediately upon the application of PEEP, tonic activities in the NTS and dl-pons elicit the Hering-Breuer reflex prolongation of expiration and shortening of inspiration, momentarily impairing entrainment. Finally, as shown in FIG. 4c, habituation of the NTS and desensitization of the pneumotaxic center eventually buffer the effect of PEEP, restoring the respiratory rhythm. Sustained stimulation of dl-pons produces similar Hering-Breuer reflex and desensitization effects as PEEP.

The important role of the pons in modulating respiratory-ventilator entrainment is also demonstrated by the dampening of entrainment during pontine stimulation. The initial inhibition and adaptation of the phrenic discharge, before the entrainment bifurcated from 1:1 ratio to higher ratios, during unilateral pontine stimulation in vagi-intact animals are intriguing and are in sharp contrast to the Hering-Breuer reflex-like respiratory response and adaptation to the same stimuli after vagotomy. These salient effects indicate the existence of complex adaptive processes at the right and left pneumotaxic center whereby ipsilateral and contralateral vagal and pontine inputs are integrated bilaterally in modulating the respiratory rhythm.

Clinical Relevance

Entrainment is an important physiologic phenomenon of potential clinical significance in that it allows the spontaneous, barring voluntary, respiratory rhythm to synchronize with the ventilator naturally without any external triggering device necessary. This potent effect has not been fully exploited in current assist/support-mode ventilators that rely on patient triggering, and deserves further investigation particularly in cases where the latter is not feasible or beneficial (M. W. Beresford, N. J. Shaw, and D. Manning "Randomized controlled trial of patient triggered and conventional fast rate ventilation in neonatal respiratory distress syndrome," Archive of Disease in Childhood Fetal Neonatal, Edition 82: F14-18, 2000; J. H. Baumer, "International randomized controlled trial of patient triggered ventilation in neonatal respiratory distress syndrome." Archive of Disease in Childhood Fetal Neonatal, Edition 82: F5-F10, 2000; A. W Thille, P. Rodriguez, B. Cabello, F. Lellouche, and L. Brochard, "Patient-ventilator asynchrony during assisted mechanical ventilation," Intensive Care Medicine, 32: 1515-1522, 2006; D. C. Chao, D. J. Scheinhorn, and M. Stearn-Hassenpflug, "Patient-ventilator trigger asynchrony in prolonged mechanical ventilation," Chest, 112: 1592-1599, 1997). Entrainment has been robustly demonstrated in normal humans during wakefulness or non-REM sleep or under anesthesia (C. Graves, L. Glass, D. Laporta, R. Meloche, and A. Grassino, "Respiratory phase locking during mechanical ventilation in anesthetized human subjects," American Journal of Physiology, 250: R902-909, 1986; P. M. Simon, A. S. Zurob, W. M. Wies, J. C. Leiter, and R. D. Hubmayr, "Entrainment of respiration in humans by periodic lung inflations. Effect of state and CO(2)," American Journal of Respiratory and Critical Care Medicine, 160: 950-960, 1999), and to some extent in subjects after lung transplant (P. M. Simon, A. M. Habel, J. A. Daubenspeck, and J. C. Leiter, "Vagal feedback in the entrainment of respiration to mechanical ventilation in sleeping humans," Journal of Applied Physiology, 89: 760-769, 2000) suggesting that other respiratory-related afferents, such as those from the chest wall, may be recruited after vagotomy to maintain entrainment. Typically, the entrained inspiratory activity precedes or lags behind machine inflation depending on whether spontaneous respiratory frequency is higher or lower than the ventilator frequency (P. M. Simon, A. S. Zurob, W. M. Wies, J. C. Leiter, and R. D. Hubmayr, "Entrainment of respiration in humans by periodic lung inflations. Effect of state and CO(2)," American Journal of Respiratory and Critical Care Medicine, 160: 950-960, 1999). Therefore, suitable choice or servo-control of ventilator frequency to match the spontaneous respiratory frequency is crucial for optimal ventilatory unloading, as significant phase shift in the entrained respiratory activity may decrease ventilatory efficiency and increase patient discomfort.

Although the important role of phasic lung volume input in mediating respiratory-ventilator entrainment is well established, the efficacy of the Hering-Breuer reflex in humans remains controversial. It has been suggested that acute lung inflation or elevation of end-expiratory lung volume or local anesthetic blockade of the vagi has little or no immediate effect on the respiratory rhythm in awake or sleeping humans (J. G. Widdicombe, "Respiratory reflexes in man and other mammalian species," Clinical Science, 21: 163-170, 1961; A. Guz, M. I. Noble, D. Trenchard, H. L. Cochrane, and A. R. Makey, "Studies on the vagus nerves in man: Their role in respiratory and circulatory control," Clinical Science, 27: 293-304, 1964; R. D. Hamilton, A. J. Winning, R. L. Horner, A. Guz, "The effect of lung inflation on breathing in man during wakefulness and sleep," Respiratory Physiology, 73:

145-154, 1988; R. D. Hamilton, R. L. Horner, A. J. Winning, A. Guz, "Effect on breathing of raising end-expiratory lung volume in sleeping laryngectomized man," Respiratory Physiology, 81: 87-98, 1990), even though pulmonary stretch receptor activity remains intact (A. Guz, D. W. Trenchard, "Pulmonary stretch receptor activity in man: a comparison with dog and cat," Journal of Physiology, 213: 329-343, 1971) and the Hering-Breuer reflex has been shown to exert significant influence on the expiratory duration in humans (H. Gautier, M. Bonora, J. H. Gaudy, "Breuer-Hering inflation reflex and breathing pattern in anesthetized humans and cats," Journal of Applied Physiology, 51: 1162-1168, 1988; S. Tryfon, T. Kiontakiotis, E. Mavrofridis, D. Patakas, "Hering-Breuer reflex in normal adults and in patients with chronic obstructive pulmonary disease and interstitial fibrosis," Respiration, 68: 140-144, 2001). For patients with acute respiratory distress syndrome the application of PEEP is needed in order to prevent lung collapse, and hence activation of the Hering-Breuer (inflation) reflex is unlikely unless the PEEP level is excessive. At any rate, the results of the present study suggest that any tonic volume-related influence on the respiratory rhythm, if at all present, may be rendered ineffective by nonassociative learning via pneumotaxic and extra-pontine pathways. Thus, respiratory-ventilator entrainment should be robust to tonic vagal input in the face of PEEP regardless of whether the Hering-Breuer reflex is fully active or not, a desirable effect that is particularly beneficial in the clinical application of mechanical ventilation.

Although the important role of the pneumotaxic center in averting apneustic breathing has been extensively documented in vagotomized animals since the discovery of this brainstem structure over eight decades ago (T. Lumsden "Observations on the respiratory centres in the cat," Journal of Physiology London, 57: 153-160, 1923), clinical case reports of apneusis are rare and often with causes unrelated to the pneumotaxic center (M. J. Mador and M. J. Tobin, "Apneustic breathing. A characteristic feature of brainstem compression in achondroplasia," Chest, 97: 877-883, 1990; Y. Saito, T. Hashimoto, H. Iwata, K. Takahashi, and M. Fukumizu, et al., "Apneustic breathing in children with brainstem damage due to hypoxic-ischemic encephalopathy," Developmental Medicine and Child Neurology, 41: 560-567, 1999). The present results provide the first direct experimental evidence demonstrating an important role for desensitization in the pneumotaxic center and habituation in extra-pontine pathways in a routine clinical setting pertaining to the management of mechanical ventilation under PEEP, absent apneusis.

Entrainment-Based Mechanical Ventilation Mechanism

Figure 5:
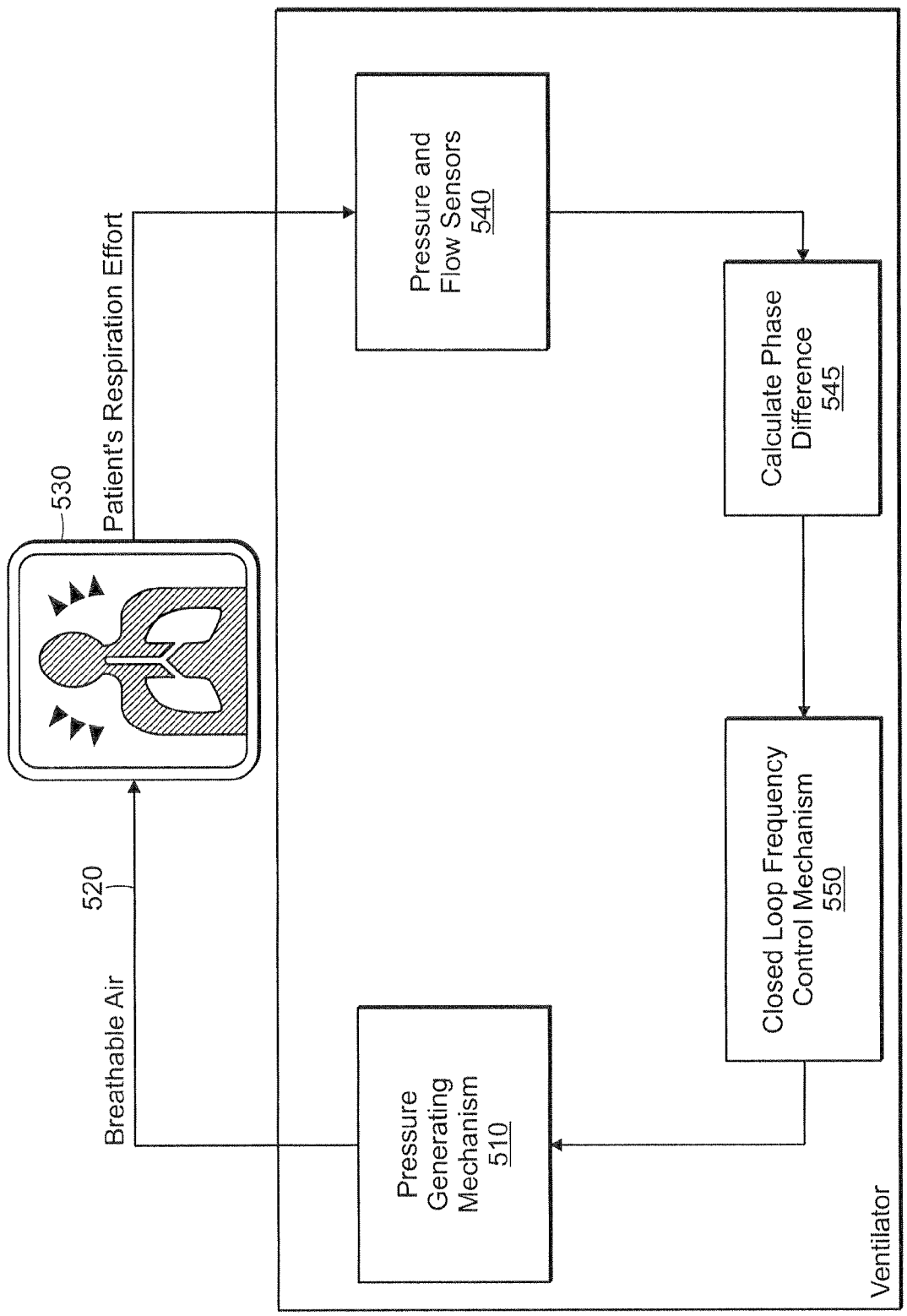
FIG. 5 demonstrates a flow chart of an example embodiment of the mechanical ventilator.

FIG. 5 is a flow diagram of an example embodiment of the mechanical ventilator 500 of this invention. In this example embodiment a pressure generating mechanism 510 pumps breathable air 520 into and out of a patient's respiratory system 530 at a ventilator-driven frequency. Pressure and flow sensors 540 sense the patient's respiration effort based on air pressure flow circulating through the patient's respiratory system. The sensors 540 may employ concepts known in art such as a first order equation of motion to obtain models for describing factors such as air flow, pressure through the patient's respiratory system, and respiratory pressure output (Chi-Sang Poon, "Control of exercise Hyperpnoea during assisted breathing", Ph.D. thesis, UCLA School of Engineering, 1981). The models obtained can then be solved to approximate factors such as a patient's respiratory effort, respiratory frequency, and tidal volume.

The ventilator 500 settings are initially set to match the patient's respiration. If the ventilator 500 is operating at the same level as the patient's respiration or is within a reasonable range from it, the patient should be able to entrain to the ventilator. Under conditions where the ventilator 500 is operating at higher or lower levels comparing to the patient's respiration, the patient will fall out of phase. The ventilator phase relative to the patient's breathing effort is calculated 545 as a function of the difference between the ventilator and the patient's respiration. Based on the phase difference, a closed-loop control mechanism 550 automatically adjusts the frequency of the pressure generating mechanism 510 to the patient's respiration. Patient-ventilator entrainment will occur when the ventilator 500 is operating at a level within a certain range of the patient's respiration.

Nonassociative learning of the respiratory system allows the patient to adapt to changes in PEEP level, ensuring continued entrainment.

Figure 6:
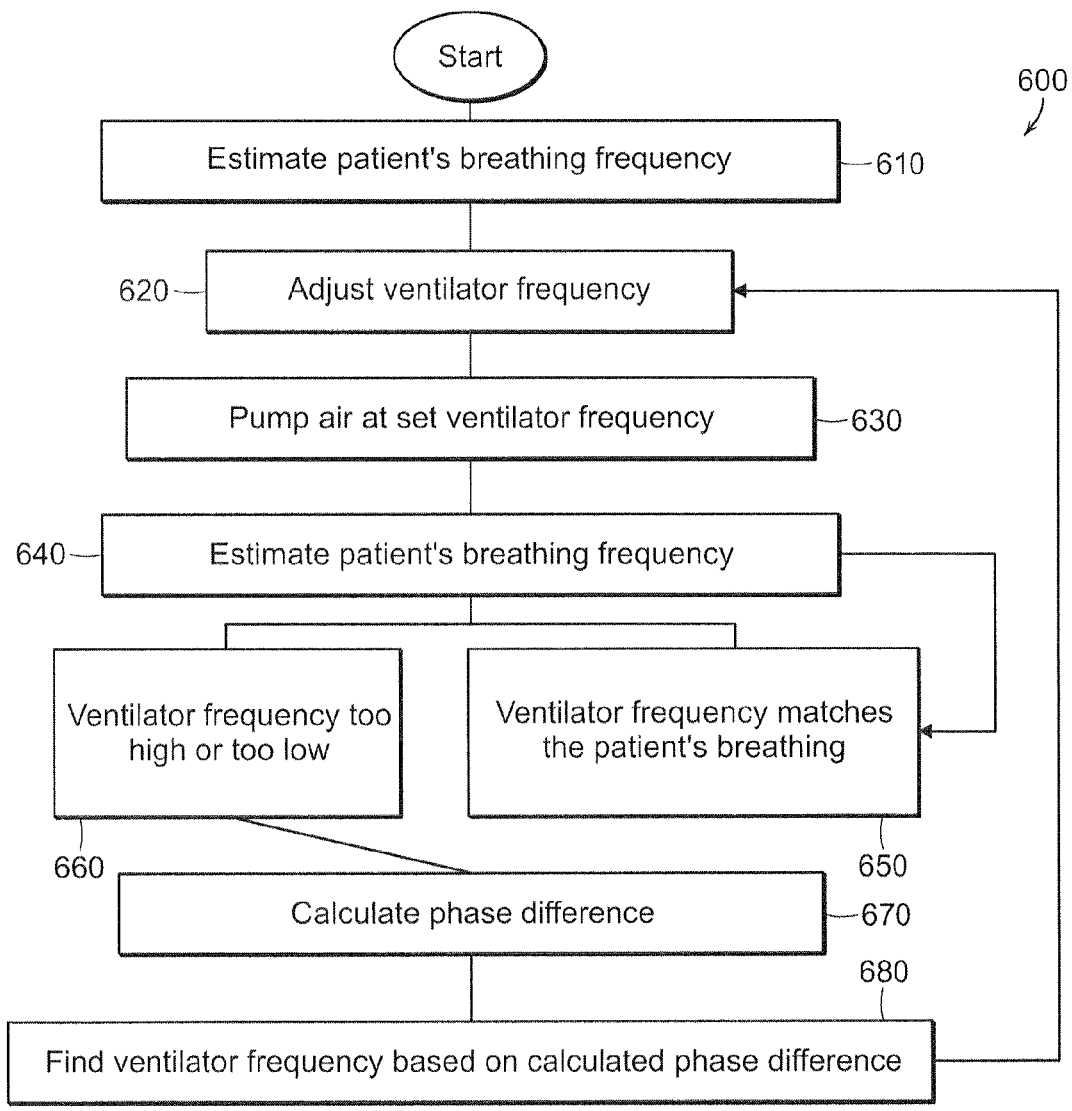
FIG. 6 demonstrates a detailed flow chart of an example embodiment of the mechanical ventilator.

FIG. 6 demonstrates a detailed flow chart of an example embodiment of the ventilation mechanism 600 of this invention. In this example embodiment, a sensing system senses the patient's respiration effort based on air pressure flow circulating through the patient's respiratory system. Based on the sensed air pressure flow, the frequency of a patient's respiration 610 may be approximated. Based on the approximated breathing frequency, the settings of the entrainment-based mechanical ventilation mechanism may be initially set to approximate the patient's spontaneous respiratory frequency and tidal volume 620, in which case the ventilator may generate breathing air at this approximated frequency to the patient 630. The sensing system subsequently measures the breathing frequency of the patient 640. If the ventilator frequency matches the patient's spontaneous breathing frequency or is within a reasonable range from it 650, the patient should be able to entrain to the ventilator. If the preset frequency of the ventilator is set too high or too low from the spontaneous frequency, the patient will fall increasingly out of phase and "fight" the ventilator 660. In this case, the ventilator calculates the ventilator phase relative to the patient's breathing effort 670 according to:

$$\text{Phase} = F(f_{Ventilator} - f_{Patient's\ respiration})$$

where $f_{Ventilator}$ denotes the frequency of the ventilator, $f_{Patient's\ respiration}$ denotes the frequency of the patient's respiration, and Phase indicates that the phase difference is calculated as a function (i.e., $F(\cdot)$) of the difference between the ventilator frequency and spontaneous frequency. Based on the phase difference, a closed-loop control mechanism may continuously adjust the ventilator frequency to match the patient breathing frequency until the phase shift is within a preset limit 680. Patient-ventilator entrainment will occur when the ventilator frequency is within a certain range from the patient breathing frequency.

Non associative learning of the respiratory system allows the patient to adapt to changes in PEEP level, ensuring continued entrainment.

Commercial Applications

Entrainment-based ventilation overcomes some of the difficulties of conventional mechanical ventilation in that it allows the patient and the ventilator to adapt in order to entrain to one another, hence greatly improving patient-ventilator synchrony and obviating the need for sedation or paralysis. It is also less costly and much easier to use than patient-triggered assisted ventilators, which often require complex servo-control mechanisms. By exploiting the patient's intrinsic ability to adapt through nonassociative learning and to entrain through couple-oscillator nonlinear dynamics, entrainment-based ventilators can ensure patient-ventilator synchrony without resorting to patient-triggered assisted ventilation.

While this invention has been particularly shown and described with references to example embodiments thereof, it will be understood by those skilled in the art that various changes in form and details may be made therein without departing from the scope of the invention encompassed by the appended claims.

What is claimed is:

1. A system comprising:
a patient ventilator, the patient ventilator including:
a positive pressure generating mechanism in the patient ventilator configured to move breathable gas into and inflate a patient's respiratory system at a ventilator driven frequency, the patient ventilator continuously cycling at the ventilator driven frequency;
a sensor in the patient ventilator sensing respiration of the patient to measure a breathing frequency of the patient; and
a closed-loop frequency control mechanism in the patient ventilator to automatically adjust the ventilator driven frequency of the positive pressure generating mechanism to the respiration of the patient to reduce a difference between the ventilator driven frequency of the positive pressure generating mechanism and the measured breathing frequency of the patient, and to entrain the patient and the patient ventilator to one another.

2. The system of claim 1 wherein the closed-loop frequency control mechanism in the patient ventilator enforces an initial frequency on the positive pressure generating mechanism.

3. The system of claim 1 wherein the closed-loop frequency control mechanism in the patient ventilator reduces a phase difference between the positive pressure generating mechanism and the respiration of the patient.

4. The system of claim 1 wherein the closed-loop frequency control mechanism in the patient ventilator automatically adjusts the ventilator driven frequency to approximate the measured breathing frequency of the patient.

5. The system of claim 1 wherein the closed-loop frequency control mechanism adjusts the ventilator driven frequency of the positive pressure generating mechanism to reduce the difference between the ventilator driven frequency of the positive pressure generating mechanism and the measured breathing frequency of the patient until the difference between the ventilator driven frequency of the positive pressure generating mechanism in the patient ventilator and the measured breathing frequency of the patient is within a preset limit.

6. The system of claim 1 wherein the closed-loop frequency control mechanism automatically adjusts the ventilator driven frequency of the positive pressure generating mechanism in the patient ventilator to the measured breathing frequency of the patient without requiring any external triggering device.

7. A patient ventilation method comprising:
generating gas pressure with a positive pressure generating mechanism in a patient ventilator configured to move breathable gas into and inflate a patient's respiratory system at a ventilator driven frequency;
continuously cycling the patient ventilator at the ventilator driven frequency;
sensing respiration of the patient to measure a breathing frequency of the patient; and
automatically adjusting the ventilator driven frequency of the positive pressure generating mechanism to the respiration of the patient to reduce a difference between the ventilator driven frequency of the positive pressure generating mechanism and the measured breathing frequency of the patient, and to entrain the patient and the patient ventilator to one another, using a closed-loop frequency control mechanism in the patient ventilator.

8. The patient ventilation method of claim 7 wherein generating the gas pressure includes enforcing an initial frequency on the ventilator driven frequency of the positive pressure generating mechanism.

9. The patient ventilation method of claim 7 wherein automatically adjusting the ventilator driven frequency of the positive pressure generating mechanism to the respiration of the patient reduces a phase difference between the positive pressure generating mechanism and the respiration of the patient.

10. The patient ventilation method of claim 7 wherein automatically adjusting the ventilator driven frequency of the positive pressure generating mechanism includes approximating the measured breathing frequency of the patient.

11. The patient ventilation method of claim 7 wherein automatically adjusting the ventilator driven frequency of the positive pressure generating mechanism to reduce the difference between the ventilator driven frequency of the positive pressure generating mechanism and the measured breathing frequency of the patient includes adjusting the ventilator driven frequency of the positive pressure generating mechanism until the difference between the ventilator driven frequency of the positive pressure generating mechanism and the measured breathing frequency of the patient is within a preset limit.

12. The patient ventilation method of claim 7 wherein automatically adjusting the ventilator driven frequency of the positive pressure generating mechanism includes adjusting the ventilator driven frequency of the positive pressure generating mechanism to the measured breathing frequency of the patient without requiring any external triggering device.

13. A system comprising:
a ventilator, the ventilator including:
a pressure generating mechanism continuously operating at a ventilator driven frequency in the ventilator configured to inflate a patient's respiratory system at positive pressure;
a sensor to sense respiration of the patient to measure a breathing frequency of the patient; and
a closed-loop frequency control mechanism to automatically adjust the ventilator driven frequency to approximate the measured breathing frequency of the patient to entrain the patient and the patient ventilator to one another.

14. A method for ventilation comprising:
generating positive pressure at a ventilator driven frequency in a ventilator configured to inflate a patient's respiratory system;
sensing respiration of the patient to measure a breathing frequency of the patient; and
automatically adjusting the ventilator driven frequency to approximate the measured breathing frequency of the patient to entrain the patient and the patient ventilator to one another.

15. The system of claim 13 wherein the closed-loop frequency control mechanism automatically adjusts the ventilator driven frequency reducing a phase difference between the positive pressure generating mechanism and the respiration of the patient.

16. The method for ventilation of claim 14 wherein automatically adjusting the ventilator driven frequency reduces a phase difference between the generated positive pressure and the respiration of the patient.

* * * * *